United States Patent [19]
Collet-Billon et al.

[11] Patent Number: 5,540,229
[45] Date of Patent: Jul. 30, 1996

[54] SYSTEM AND METHOD FOR VIEWING THREE-DIMENSIONAL ECHOGRAPHIC DATA

[75] Inventors: Antoine Collet-Billon; Raoul Mallart, both of Paris, France

[73] Assignee: U.S. Philips Cororation, New York, N.Y.

[21] Appl. No.: 308,050

[22] Filed: Sep. 16, 1994

[30] Foreign Application Priority Data

Sep. 29, 1993 [FR] France .................................. 93 11609

[51] Int. Cl.$^6$ ...................................................... A61B 8/00
[52] U.S. Cl. .................................... 128/660.070; 128/916
[58] Field of Search .................... 128/660.070, 661.010, 128/916; 382/6

[56] References Cited

U.S. PATENT DOCUMENTS

| | | | |
|---|---|---|---|
| 4,613,866 | 9/1986 | Blood | 343/448 |
| 4,821,731 | 4/1989 | Martinelli et al. | 128/662.06 |
| 5,353,354 | 10/1994 | Keller et al. | 382/6 |

OTHER PUBLICATIONS

Innovation Et Technologie En Biologie Et Medecine, vol. 13, No. 1, 1992 "Imagerie Echographique 3D" pp. 117–125. A. Collet–Billon et al.

*Primary Examiner*—Francis Jaworski
*Attorney, Agent, or Firm*—Jack D. Slobod; Edward Blocker

[57] ABSTRACT

A system useful echographic examination simulation and training includes an ultrasonic echograph (31) equipped with a TV monitor (32), a 3D probe (33) for analyzing a subject, acquisition means (39), a memory card (42) storing the detected acoustic lines and a workstation (34) with central processing unit (35) and 3D echography memory (38). For reading the latter memory (38), the system includes a viewing device including a dummy (56) simulating the subject, and a 3D orientation sensor (52) connected to the workstation via a 3D coordinate indicator (54) and display means (29) of the workstation, which make the sectional plane which the sensor defines on the dummy correspond to the equivalent plane contained in the form of voxels in the echography memory (38), and display this plane on the screen of the TV monitor (32).

11 Claims, 2 Drawing Sheets

SYSTEM AND METHOD FOR VIEWING THREE-DIMENSIONAL ECHOGRAPHIC DATA

FIELD OF THE INVENTION

The present invention relates to a three-dimensional (3D) echography system, including a host ultrasonic echograph equipped with a TV monitor, an ultrasonic probe with 3D scanning connected to the echograph, for analyzing a subject, first electronic acquisition means which include a control card in charge of the azimuth scanning of the probe and a memory card storing the acoustic lines originating from the echograph, a workstation consisting of a microprocessor assembly equipped with an echography memory for storing 3D echographic data on the subject, the probe, the electronic means and the workstation being linked together by a specific bus.

More generally, the subject of the invention is a method of 3D echography consisting, in the first place, in performing the acquisition of echographic lines distributed in a volume and passing through the point of application of a 3D echographic probe against a subject, in converting these lines into the form of digital volumetric image elements (voxels), identified in spherical coordinates, then in converting the coordinates of the said voxels into Cartesian coordinates.

DESCRIPTION OF THE RELATED ART

Traditional medical echography consists in forming, in real time, images of biological structures (of a subject) by using ultrasound as an information source. To do that, a plane identical to the emission plane is chosen as the plane of reception of the echo, while illuminating the chosen subject by a very brief signal. Advantage is then taken of distance information to locate the non-uniformities in the subject in the emission/reception plane through the radius and the center of curvature of the reflected wavefront, and also by taking account of the time $\tau$ of arrival of the start of this wavefront at the reception plane:

$$\tau = 2z/C$$

z: distance from the target to the emission/reception plane
C: speed of propagation of ultrasonic waves in an aqueous medium (1540 m/s).

A shot can thus be taken in a direction substantially perpendicular to the emission/reception plane. In order to produce an image, it is sufficient to repeat the shots while regularly moving the probe so as to obtain the required information. In preference, angular displacement is carried out in a plane, perpendicular to the emission/reception plane, which constitutes a sectional plane of the subject to be viewed, in such a way as to obtain the echographic data in polar coordinates, the nose of the probe remaining applied at the same spot against the subject. Sectorial scanning in the sectional plane is generally performed electronically, at a fast frequency, so that, at any instant, it is possible to display, on the TV monitor associated with the echograph, the echographic contents of the sectional plane seen by the probe, that is to say a plane passing through the axis of symmetry of the probe which is described as two-dimensional (or 2D probe). The use, in the probe, of linear arrays of transducers makes it possible, by rapid electronic switching, to achieve a high image rate, of the order of 50 images per second, i.e. the possibility of real-time imaging.

Starting from this technological background, which remains in accordance with the usual practices of the practitioner who thus always performs an echographic analysis by displacing the probe against the body of a patient, it is now known to perform three-dimensional echography which, using three-dimensional (or 3D) probes, allows rapid acquisition of echographic data of a predetermined volume portion of a subject. In order to do this, a specific 3D probe is preferably used, consisting of two-dimensional, sectorial, annular arrays and including electronic and mechanical means respectively for performing first and second crossed sectorial scans respectively, the probe emitting at a frequency lying between 3 and 8 MHz.

As an echograph to be fitted to the 3D probe for acquiring volumetric data, identified from now on in spherical and no longer polar coordinates, it is possible to use an extension of a high-performance 2D system. In addition to one or more 3D probes, this system further includes acquisition electronics in control of the scanning along the third (azimuthal) dimension and of the position-locating of the probe in this direction, and a unit for control of the system and for 3D data processing. The latter is a workstation consisting of a microprocessor, fitted with its usual peripherals. Its task is, on the one hand, the control of the system and, on the other hand, the post-processing of the volumetric data, in particular a first operation which consists in converting into a Cartesian coordinate scan the 3D data previously acquired in spherical coordinates.

The above-mentioned hardware is described, in more detail, in the journal: "Innovation et Technologie en Biologie et Médecine" [Innovation and Technology in Biology and Medicine], Vol. 13, Special No. 1, 1992, in the article: "Imagerie échographique 3D" ["3D echography imaging"], pages 117 to 125, by Messrs A. Collet-Billon, Y. Le Gu érinel, F. Bernard, and J. M. Levaillant.

The procedure for using this hardware unfolds in successive phases.

In a first exploration phase, the 3D probe is used as a conventional 2D probe, offering the same possibilities for real-time imaging on the screen of the monitor of the 2D–3D echograph indicated above. The user searches for the best position of the probe and checks the contents of the region explored by modifying the incidence of the scanning plane with the aid of knobs on the probe.

The acquisition phase which follows is triggered by pressing on another knob. The probe then automatically scans the volume in a few seconds. For this duration, any movement of the probe or of the patient must be avoided.

After the acquisition, the data are transferred to the workstation in a few seconds. The user can then delimit a region of interest in the data acquired, before running the scan conversion, an operation which consists in converting the spherical geometry of the acoustic lines into a Cartesian geometry which is better adapted to the visual display.

Next the interpretation of the data can take place: the user can view the volumetric data via a graphics user interface, completely controllable by a conventional mouse. In particular, any section, of arbitrary orientation, may be obtained simply from anatomical reference points (3 points) designated with the mouse. Views known as hidden views, that is to say which are perpendicular to the direction of the echographic shot, and usually inaccessible with a 2D echograph, can be easily obtained. Dynamic sequences of repeat sections, from front to back or in rotation, can also be viewed. The multi-sectional views allow rapid inspection of the 3D vicinity of any point of the data set. In the same session, images obtained from several data sets can be displayed simultaneously and compared, etc. All these possibilities for display, for rendering volume in perspective, and yet others are within the scope of the person skilled in the art, guided by the practitioner who himself has a medical training. However, the 3D echographic data contained in the workstation might conceivably be interpreted in a way which is completely adapted to the customs and practices of the echographist, and the latter might be provided with means for exploring the said 3D echographic data by making exactly the same movements as for a conventional, real-time, 2D echographic exploration, this constituting the basic idea of the invention.

Without prejudice to the known mode of interpreting 3D echographic data described above, the invention aims to solve the technical problem which consists in being able fully to exploit the experience and the competence of a practicing echographist without having to trouble him or her with the running of a workstation for which he or she may not have been trained, and by means of which he or she would obtain an insufficiently interactive visual display, or at the very least an unfamiliar one.

Still within the context of the visual display of 3D echographic data, another subject of the invention, which determines the main application of the latter, is a learning aid for real-time, 2D echographic examination, learning to do such examination is a lengthy process and difficult as it is often subject to faulty interpretations. As this learning may, according to the invention, take place off-line, without the presence of a patient, it becomes possible to devote a great deal of time to it, to make repetitive manipulations and, as the 3D data are fixed, to carry out, for example, a systematic search on sections which would be determined in advance by an instructor practitioner. Moreover, several students can work at the same time on the same 3D database.

SUMMARY OF THE INVENTION

The above-mentioned technical problem is solved since that the 3D echography system defined in the first paragraph is noteworthy in that it further includes, for reading the said echography memory, a device for viewing the data in the said echography memory, consisting, on the one hand, of a dummy which simulates the said subject, and, on the other hand, of a 3D orientation sensor connected to the workstation via a 3D coordinate indicator, and second electronic display means in the said workstation, which, at each position of the said sensor to be manipulated like a two-dimensional (2D) echographic probe simulator in proximity to the dummy, make the sectional plane which the sensor defines towards the dummy correspond to the equivalent plane contained in the form of volumetric image elements (voxels) in the echography memory, and which display this plane on the screen of the said TV monitor.

Likewise, the method of 3D echography defined in the second paragraph is noteworthy in that the viewing of the said voxels in Cartesian coordinates, in the form of sectional planes, takes place by simulation of a 2D echography session or sessions, by conventional manipulation of an 3D orientation sensor, which simulates a 2D echography probe against a dummy which is simulating the said subject, a predetermined homothetic ratio being established between the size of the subject and that of the dummy, and the addressing of the said voxels, in the form of sectional planes through the volume which the said voxels represent, being proportional to the variations in displacement and in orientation of the said sensor against the said dummy.

The 3D orientation sensor, which here replaces the mouse usually connected to the workstation, or which is linked to the workstation in addition to the latter by way of an additional peripheral, is preferably of the type with three electromagnetic coils which detect the magnetic fields emitted by a fixed source emitter arranged in proximity to the said dummy, the said sensor and the said source emitter being connected to electronic equipment which is itself connected to the said workstation.

Such a sensor, accurate both in spatial position and in angular position of precession, of nutation and of characteristic rotation, is manufactured especially by the American Company Polhemus, P.O. Box 560, Colchester, Vt. 05446 or also by the American company Ascension Technology Corp. P.O. Box 527, Burlington, Vt. 05402.

The description which follows, with regard to the attached drawings, all given by way of example, will make it clear how the invention can be carried out.

DESCRIPTION OF THE PREFERRED EMBODIMENTS

Figure 1:
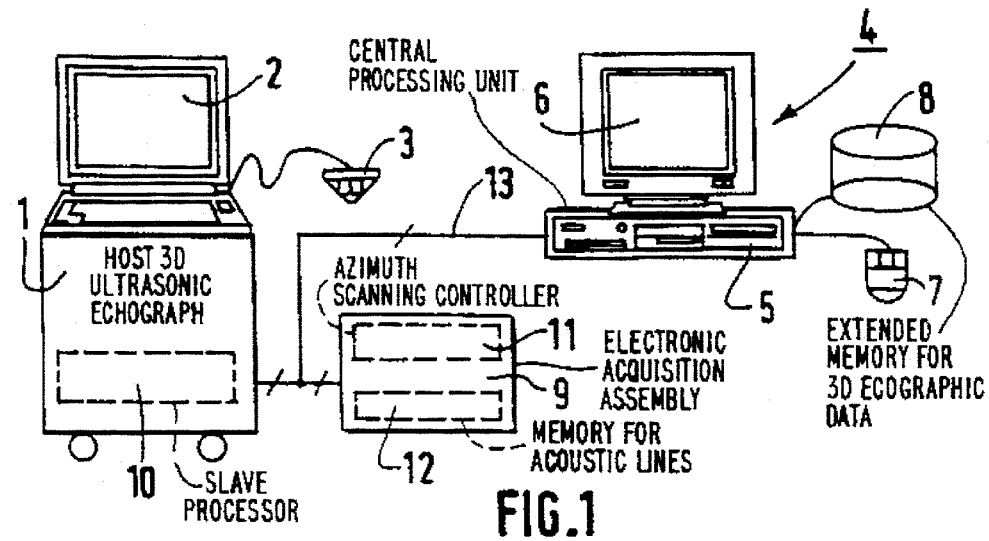
FIG. 1 represents a 3D echography system as in the state of the art.

The system of FIG. 1 allows the exploration of echography data distributed in a volume. It consists of an extension of a top-of-the-range 2D echograph. This system includes a 3D ultrasonic host echograph, 1, which is essentially a 2D echograph, equipped with a TV monitor, 2, which allows real-time display of sections taken in conventional 2D echography in the course of the analysis of a subject.

For adapting to 3D, the conventional 2D probe is, in the first place, replaced by one or more 3D probes, such as 3, able to carry out an additional scanning in azimuth, associated with electronic control means (not represented). A workstation 4 consists of a central processing unit 5 and of its usual peripherals, such as the monitor 6 and the mouse 7. The workstation adopted is a "SUN" machine for example the "SUN SPARC 2", with an extended memory shown symbolically at 8, a large disk space and an Exabyte unit. Its task is, on the one hand, the control of the system, and, on the other hand, the post-processing of the volumetric data. Moreover, an electronic acquisition assembly 9 is also necessary, when changing from two-dimensional to three-dimensional, which includes a control card 11 in charge of the additional scanning and of the recording of the azimuth positions of the probe, as well as a memory card 12 for storing the demodulated and digitized acoustic lines originating from the echograph 1. A specific bus 13 links the elements 1, 9 and 4 in pairs and bidirectionally. This takes the form, for example, of a VME bus.

The 3D probes used, such as 3, are preferably 2D sectorial annular arrays, an extension of the conventional 1D annular arrays. The annular arrays offer a decisive advantage with respect to the other probes (linear arrays included): the possibility of position location-tracking in the out-of-plane direction, that is to say perpendicular to the plane of the image, i.e. the possibility of controlling the sectional thickness over the whole field explored. In order to facilitate acoustic access to the organs examined, the imprint of the nose of the probe is as small as possible; its design minimizes reverberation. Moreover, in contact with the skin of the patient during the acquisition, which is done in spherical coordinates, the nose of the probe remains immobile; there is therefore no movement of tissues which would be caused by sweeping. Three knobs make it possible to control the successive phases of an acquisition. In preference, the usual 2D sectorial scanning is done by electronic means, and the crossed azimuthal sectorial scanning by mechanical means.

To the electronic acquisition assembly 9 it is appropriate to add a slave processor card 10 inserted in a rack of the echograph 1, which makes it possible to obtain the acoustic lines immediately after they have been digitized, as well as the various synchronization signals necessary. The manual 2D scanning of the annular array is taken charge of by the host echograph.

The workstation includes dedicated software, within the scope of the average information technologist, which is, preferably, organized into 5 modules: exploration-configuration, acquisition, 3D scanning conversion, visual display, archiving and management of the system. The method of using the system of FIG. 1 unfolds in successive phases which have already been described above before the description of the figures.

Concerning the acquisition phase, the echograph functions sequentially, that is to say that an acoustic shot is triggered only after reception of the preceding acoustic line. Considering a data set whose line density is similar in the plane of the image and in elevation, and with identical angular aperture in these two directions (about 90°), the total number of acoustic lines is of the order of 100×100. Assuming that the depth of acquisition is 20 cm, the minimum acquisition time is 2.7 s, owing to the speed of sound in the tissues (1540 /ms on average). The acoustic lines, digitized, are stored in the memory 12.

After the acquisition, a series of images which are reconstructed from raw data is displayed on the screen 6 of the workstation, so as to check that the acquisition phase has taken place correctly. If so, the data are transferred from the memory 12 to the workstation in a few seconds. A region of interest is then selected in the data acquired, then spherical coordinate Cartesian coordinate scanning conversion is triggered, for this region, for the volumetric pixels (or voxels) selected and stored in memory at 4.

At this stage, the interpretation of the echographic data can be carrried out, by any known means, especially by means of the mouse 7.

The simplest means for seeing the 3D data on a 2D screen consists in offering the possibility of displaying sections in the volume acquired, along any orientation, in real time. A tomographic section is, in fact, an image which the echographist is accustomed to interpreting. When he uses the echograph, the doctor searches for the most favorable orientations of the probe, that is to say those which contain relevant clinical information; this mode of use is only possible in practice because the echograph offers an image rate said to be in "real time", i.e. from 10 to 50 images per second.

The system according to the invention which is described below makes it possible, especially for the doctor, to perform scanning through 3D data previously acquired on a virtual patient, that is to say a dummy or a phantom, in the same way as if it related to a real-patient environment.

Figure 2:
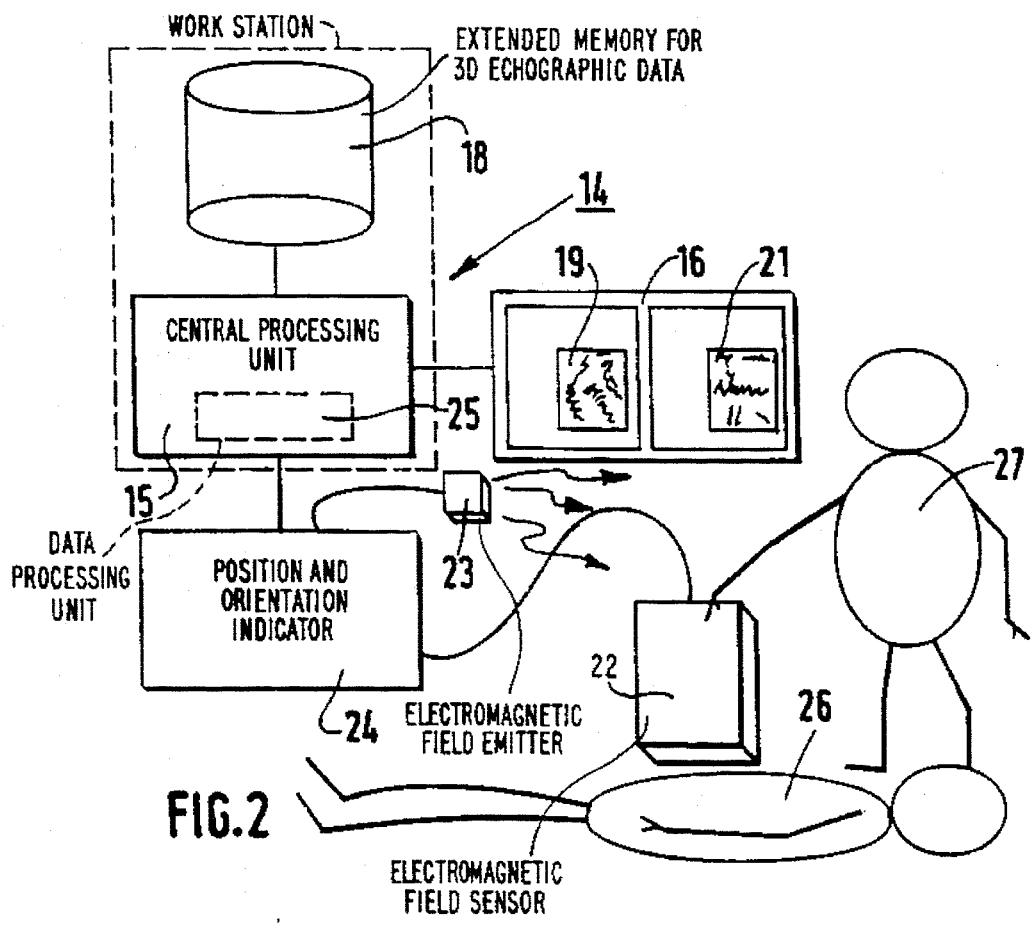
FIG. 2 shows the basic principle of the invention.

FIG. 2 makes it possible to explain the basic principle of the invention. A workstation 14, comparable to the station 4, includes a central processing unit 15 with a memory 18 and a monitor 16. The memory 18 contains data on a subject, distributed in a volume (3D data or voxels), which are addressable in Cartesian coordinates, and from which sections 19, 21 can be displayed on the of monitor 16, by any known means, especially by means of a keyboard or of a mouse (not represented). According to the invention, for the display of the sections, by way of a 3D mouse, a distance identification device is used which, in the embodiment of FIG. 2, consists of three elements, and the essential element of which is a 3D sensor, 22, which supplies its own position in space (attitudes and coordinates, i.e. three non-coplanar angles and three distances), precisely and in real time, at the rate of 50 positions per second. The second element is a source emitter 23 which emits an (electro)magnetic field picked up by the sensor 22, the elements 22 and 23 being connected to an electronics cabinet 24, 3D position and orientation indicator (with 6 degrees of freedom), itself connected to the microprocessor 15. At 15, a dedicated processing unit 25 has the function of performing a calculation of sections, that is to say of deducing, from each sextuple position supplied by the sensor 22, a corresponding sectional plane, in a one-to-one way, so to say through the voxels contained in memory 18. More precisely, from an initial positioning point and from an initial orientation which are chosen as references, at the start, a constant homothetic ratio is established between the displacement of the point of positioning of the probe and the displacement of the reference point of the corresponding sectional plane and, in a similar way, the variations in orientation of the sensor 22 in space are faithfully reflected between the sectional planes corresponding to these variations on the screen 16. The processing unit 25, by means of appropriate programming, left to the initiative of the person skilled in the art, thus carries out a specific addressing calculation for the voxels, at 18, aiming exactly to copy the volume described by the sensor 22 in free space in proximity to the source emitter 23, to the volume stored in memory by the voxels at 18. In order to give even better concrete expression of this effect, and thus to offer a physical support for the manipulation of the sensor, it is permissible to fill the free space in question with a scaled phantom of the subject, the interior of which is imaged by the voxels from the memory 18. If the voxels constitute 3D echographic data on the body of a patient, the phantom is then a dummy 26 which represents this patient (on the scale of 1 for a homothetic ratio of 1) and the sensor will be able to be manipulated by a practitioner 27 in the same way as a 2D echographic ultrasonic probe. Advantageously, the sensor may be built into a housing, or a simulator of a housing (not represented) of such a probe. Thus a complete simulation of a conventional 2D echographic analysis session is obtained, from 3D echographic data, which although fixed, are real. It is also possible, simultaneously and in real time, to display several sections, for example the section which the probe would give when used conventionally and a section called C-scan, which is oriented perpendicularly to the acoustic beam (to the line of the echographic shot) and which is impossible to obtain with a conventional echograph.

Figure 3:
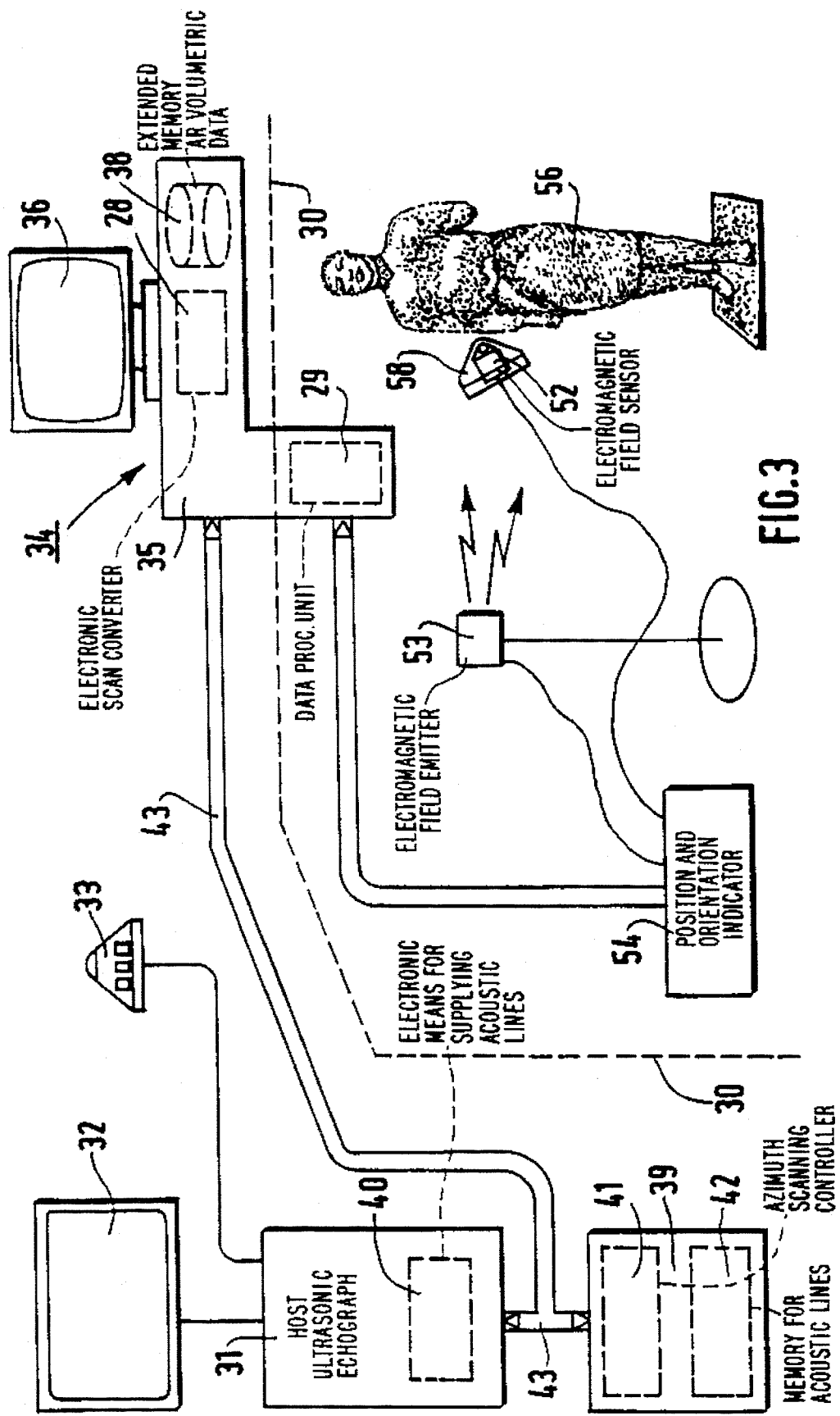
FIG. 3 is, in essence, a block diagram of the 3D echography system according to the invention.

FIG. 3 shows a preferred embodiment of the invention, applied to ultrasonic echography, in which figure are again found the majority of the elements (or equivalents) described above separately with reference to FIGS. 1 and 2. In this figure, a host ultrasonic echograph 31 equipped with a TV monitor 32 and, if appropriate, with a 2D probe (not represented) makes it possible to perform conventional 2D echographic analysis. In order to adapt it to 3D echography, it further includes a 3D probe, 33, of any known type, electronic means 40 (called third electronic means) for supplying acoustic lines measured by the probe 33. The echograph 31 is associated moreover with first electronic acquisition means 39 which include a control card 41 equivalent to the control card 11 of FIG. 1 and a memory card 42 equivalent to the memory card 12 of FIG. 1. A workstation 34, equivalent to 4, allows management of the above-mentioned 3D echographic system, a specific bus 43 linking the elements 31, 39 and 34, in pairs and bidirectionally. The workstation 34, including a microprocessor 35 and a screen 36, is equivalent, as to its structure, to the workstations 4, FIG. 1, or 14, FIG. 2 and its functions constitute a hybridization of the functions described for 4, FIG. 1 and for 14, FIG. 2. The central processing unit 35 includes electronic scanning conversion means 28, called fourth electronic means, a 3D echography memory, 38, and electronic data processing means 29, called second electronic means, equivalent to the processing unit 25, FIG. 2. These second electronic means, as well as the other elements situated below and to the fight of a dashed line 30 constitute the core of the invention. The 3D sensor, 52, the source emitter 53, the 3D position and orientation indicator, 54, and the dummy 56 are equivalent to the respective elements 22, 23, 24, 26 of FIG. 2. The reference 58 designates a housing or a simulator of a housing of a 2D ultrasonic echographic probe.

When it is desired, with the system indicated above, to make a simulation of a 2D echographic analysis, it is necessary to set the sensor 52 to its origin with respect to the dummy 56. In fact, one orthonormal axis system ox, oy, oz is associated to the sensor, and another one is associated to the source 53. In order to set the sensor to the origin, it is necessary to place two orthogonal three-axes reference systems, with their corresponding axes parallel pairwise, which provides the zero for the angles. Moreover, with a predetermined sectional plane taken as origin, in memory 38, and displayed on the monitor 36, it is necessary to associate the corresponding point with the above-mentioned orientation, for the position of the sensor, with respect to the dummy 56. (It relates, for example, to a plane which passes in the middle of the voxels, at 38, following a pre established, privileged axis). By initializing the system for this origin position, the angular and spatial zero sought is obtained, on the basis of which the real-time 2D simulation will be able to be performed, all the subsequent movements of the probe then being measured with respect to this starting position. The additional degree of freedom which is the variable homothetic ratio offered by the system, as already set out above is, for its part, fixed in advance, by programming (easy, for the person skilled in the art) with, possibly, a prior calibration, in order to obtain as close a correspondence as possible between the voxels of the dummy seen by the sensor 52 and the corresponding voxels contained in the memory 38, from original sectional planes coinciding during the zero-setting.

The invention is not intended to be limited to the embodiments described above. In fact, the 3D data collected in the memory 8, 18 or 38 could be of any other nature than data of ultrasonic origin, obtained by echography. They could, in particular, be synthetic voxels representing a figurative, or other, three-dimensional image. The dummy which, in every case, is to give a visual image of the envelope of the volume represented by the voxels, could, in particular, be a hologram. Moreover, the sensors with their associated electronics, other than those described above, are usable, such as for example a 3D sensor with gyroscope, or orientation indexing devices based on the principle of reflection of acoustic waves from obstacles or surrounding walls, picked up by several microphones, or also based on a triangulation obtained on the basis of several cameras which continuously film the 3D sensor.

On the applications front, in addition to the applications to real-time 2D echography described above, the invention is of interest in teaching, for example for the study of human or animal anatomy or of botany, or for popularizing science, by making it possible, in a simple manner, to view the section of a model seen along any angle whatever.

We claim:

1. A 3D echography system, comprising a host ultrasonic echograph equipped with a TV monitor, a ultrasonic probe connected to said echograph, for analyzing a subject, first electronic acquisition means which include a control card for controlling azimuth scanning of the probe and a memory means for storing acoustic lines originating from the echograph, a workstation comprising a processing unit equipped with an echography memory for storing 3D echographic data on the subject as voxels, the probe, the first electronic means and the workstation being linked together by a bus, wherein the system further includes, for simulation of a 2D echography session or sessions, a dummy which simulates the subject and a 3D position and orientation sensor connected to the workstation, via a 3D position and orientation indicator, and second electronic display means contained in said workstation, which, at each position of said sensor to be manipulated as a 2D echographic probe simulator in proximity to the dummy, makes a sectional plane which the sensor defines towards and into the dummy correspond to an equivalent plane contained in the form of voxels in the echography memory, and which displays this plane on the screen of said TV monitor.

2. A 3D echography system according to claim 1, in which said ultrasonic probe comprises 2D, sectorial, annular arrays and includes second electronic and mechanical means respectively for performing first and second crossed sectorial scans respectively, the said probe emitting at a frequency lying between 3 and 8 Mhz.

3. A 3D echography system according to claim 2, in which said host echograph is a 2D echograph which includes third electronic means for supplying 3D acoustic lines after they have been digitized, and synchronization signals, and in which said workstation includes third electronic means for converting the 3D data previously acquired in spherical coordinates into a Cartesian-coordinate scan.

4. A 3D echography system according to claim 2, wherein said 3D orientation sensor has three electromagnetic coils which detect the magnetic fields emitted by a fixed source emitter arranged in proximity to said dummy, said sensor and said source emitter being connected to said 3D coordinate indicator.

5. A 3D echography system according to claim 1, in which said host echograph is a 2D echograph which includes second electronic means for supplying 3D acoustic lines after they have been digitized, and synchronization signals, and in which said workstation includes third electronic means for converting the 3D data previously acquired in spherical coordinates into a Cartesian-coordinate scan.

6. A 3D echography system according to claim 5, wherein said 3D orientation sensor has three electromagnetic coils which detect the magnetic fields emitted by a fixed source emitter arranged in proximity to said dummy, said sensor and said source emitter being connected to said 3D coordinate indicator.

7. A 3D echography system according to claim 1, characterized in that said 3D orientation sensor has three electromagnetic coils which detect the magnetic fields emitted by a fixed source emitter arranged in proximity to said dummy, said sensor and said source emitter being connected to the said 3D coordinate indicator.

8. A method of 3D echography, comprising performing the acquisition of echographic lines distributed in a volume and passing through the point of application of a 3D echographic probe against a subject, converting these lines into the form of digital voxels identified in spherical coordinates, then converting the coordinates of the said voxels into Cartesian coordinates, and viewing said voxels in Cartesian coordinates, in the form of sectional planes, by simulation of a 2D echography session or sessions, by manipulation of a 3D position and orientation sensor, which simulates a 2D echographic probe against a dummy which is simulating said subject, a predetermined homothetic ratio being established between the size of the subject and that of the dummy, and addressing said voxels, in the form of sectional planes through the volume which said voxels represent, being proportional to the variations in displacement and in orientation of said sensor against said dummy.

9. A method of 3D echography according to claim 8, wherein said homothetic ratio is equal to 1.

10. A method of generating a two-dimensional image from volumetric image data stored in a digital memory, which image data represents the interior of a subject of a particular type, said method comprising:

placing a probe proximate the surface of an object which simulates said subject;

sensing the position and orientation of said probe; and generating a two-dimensional image from the stored volumetric image data in dependence on the sensed position and orientation of said probe, which image represents the interior of the subject in a sectorial plane directed towards and into the subject from a position relative to the subject equivalent to the position of the probe relative to said object.

11. A method as claimed in claim 10 further comprising the initial step of acquiring and storing said volumetric image data in said memory in response to detecting radiation exiting said subject.

* * * * *